United States Patent [19]
Aida et al.

[11] Patent Number: 5,994,291
[45] Date of Patent: Nov. 30, 1999

[54] (E)-(R)-2-ALKYL-4-(2,2,3,-TRIMETHYLCYCLOPENT-3-EN-1-YL)-2-BUTEN-1-OL, PROCESS FOR PREPARING THE SAME, AND USE THEREOF

[75] Inventors: Takashi Aida; Makoto Harada; Takeshi Yamamoto; Hisao Iwai; Akira Amano; Tetsuro Yamasaki, all of Kanagawa, Japan

[73] Assignee: Takasago International Coporation, Tokyo, Japan

[21] Appl. No.: 08/927,684

[22] Filed: Sep. 11, 1997

[30] Foreign Application Priority Data

Sep. 17, 1996 [JP] Japan .................................. 8-244842
Apr. 16, 1997 [JP] Japan .................................. 9-098760

[51] Int. Cl.$^6$ ...................................................... A61K 7/46
[52] U.S. Cl. ................................................ 512/8; 568/838
[58] Field of Search ................................. 568/838; 512/5, 512/8

[56] References Cited

U.S. PATENT DOCUMENTS

| | | |
|---|---|---|
| 4,052,341 | 10/1977 | Naipawer et al. . |
| 4,610,813 | 9/1986 | Schulte-Elte et al. . |
| 4,696,766 | 9/1987 | Naipawer . |
| 5,512,543 | 4/1996 | Chapuis et al. . |

FOREIGN PATENT DOCUMENTS

| | | |
|---|---|---|
| 68936 | 1/1969 | Germany . |
| 55-139330 | 10/1980 | Japan . |
| 56-36176 | 8/1981 | Japan . |

OTHER PUBLICATIONS

Acree et al., "Odor Thresholds of the Stereoisomers of Methyl Jasmonate", *J Agric Food Chem* vol. 33, pp. 425–427, 1985.

Lewis et al., "Reaction of α–Pinene Oxide with Zinc Bromide and Rearrangement of 2,2, 3–Trimethyl–3–cyclopentene products Derived Therefrom", *J Org Chem*, vol. 30, pp. 4271–4275, Dec. 1965.

Reinhardt et al., "Enantiomer Separation of α–campholene and encholene derivatives by capillary gas chromatography on permethylated cyclodextrin phases", *J Chromatog A*, vol. 697, No. 7, pp. 475–484, 1995.

Reinhardt et al. J Chromatogr. A. 697 (1995) 475–484.

*Primary Examiner*—Michael L. Shippen
*Attorney, Agent, or Firm*—Sughrue, Mion, Zinn, Macpeak & Seas, PLLC

[57] ABSTRACT

An (E)-(R)-2-alkyl-4-(2,2,3-trimethylcyclopent-3-en-1-yl)-2-buten-1-ol represented by formula (I):

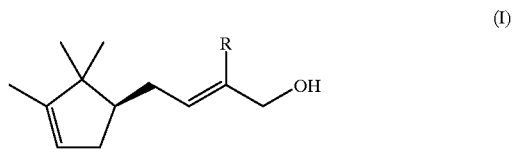

(I)

wherein R represents an alkyl group having 1 to 3 carbon atoms, and a process for preparing the same comprising hydrogenating a corresponding (E)-(R)-2-alkyl-4-(2,2,3-trimethylcyclopent-3-en-1-yl)-2-buten-1-al in the presence of a ruthenium-phosphine complex as a catalyst, a base comprising an alkali metal or an alkaline earth metal, and an amine. The compound (I) has an excellent sandalwood oil odor.

13 Claims, No Drawings

(E)-(R)-2-ALKYL-4-(2,2,3,-TRIMETHYLCYCLOPENT-3-EN-1-YL)-2-BUTEN-1-OL, PROCESS FOR PREPARING THE SAME, AND USE THEREOF

FIELD OF THE INVENTION

This invention relates to an (E)-(R)-2-alkyl-4-(2,2,3-trimethylcyclopent-3-en-1-yl)-2-buten-1-ol which is a novel optically active compound, a process for preparing the same, and a perfume composition containing the same.

An (E)-(R)-2-alkyl-4-(2,2,3-trimethylcyclopent-3-en-1-yl)-2-buten-1-ol has a fine sandalwood-like odor, and a perfume composition containing it is useful in various cosmetics, fragrances, toiletries, and other hygienic goods.

BACKGROUND OF THE INVENTION

Sandalwood oil is an essential oil obtained from sandalwood tree occurring in the east of India and is highly valued as a perfume component. However, production of sandalwood oil is being decreased because, felling of the sandalwood tree is restricted from the standpoint of environmental and resources conservation pressures. Therefore synthetic sandalwood oil fragrance materials have been developed for substitution.

It is known that the main components responsible for the odor of natural sandalwood oil are α-santalol and β-santalol. Santalol is difficult to synthesize in quantities because of its chemical structure. In recent years, substances different from santalol in chemical structure but very similar in odor to santalol have been synthesized.

Among such substances are 2-alkyl-4-(2,2,3-trimethylcyclopent-3-en-1-yl)-2-buten-1-ol derivatives (see JP-B-56-361676 and JP-A-55-139330, the term "JP-B" as used herein means an "examined Japanese patent publication", and the term "JP-A" as used herein means an "unexamined published Japanese patent application"). 2-Methyl-4-(2,2,3-trimethylcyclopent-3-en-1-yl)-2-buten-1-ol is available from Taiyo Koryo K.K. under the trade name of "Santalinol", and 2-ethyl-4-(2,2,3-trimethylcyclopent-3-en-1-yl)-2-buten-1-ol from International Flavor and Fragrance (hereinafter abbreviated as IFF) under the registered trademark "Bacdanol".

There is found no report on synthesis of an optically active 2-ethyl-4-(2,2,3-trimethylcyclopent-3-en-1-yl)-2-buten-1-ol.

R. Reinhardt, et al. have reported in *J. Chromatog. A*, Vol. 697, No. 7, pp. 475–484 (1995) that the resolution of 2-ethyl-4-(2,2,3-trimethylcyclopent-3-en-1-yl)-2-buten-1-ol was not successful by gas chromatography using a chiral column.

Thus, there is no report on the isolation or synthesis of an (E)-(R)-2-alkyl-4-(2,2,3-trimethylcyclopent-3-en-1-yl)-2-buten-1-ol, i.e., an optically active compound of a 2-alkyl-4-(2,2,3-trimethylcyclopent-3-en-1-yl)-2-buten-1-ol in which the trimethylcyclopentene ring and the hydroxymethyl group are in a trans configuration.

Several reports are found with respect to the relation between the configurations of the side chain of fragrance substances having a trimethylcyclopentene ring and the odor.

For example, (1) concerning the relation between odor and the absolute configuration of the asymmetric carbon atom on the 1-position of the cyclopentene ring in compounds having a (2,2,3-trimethyl-3-cyclopenten-1-yl) alkanol skeleton, U.S. Pat. No. 4,052,341 and U.S. Pat. No. 4,610,813 have reported that the (R)-isomer and the (S)-isomer have the same odor as the racemate, that is, the absolute configuration has no influence on odor.

(2) As for 3-methyl-5-(2,2,3-trimethyl-3-cyclopenten-1-yl)-4-penten-2-ol, U.S. Pat. No. 4,696,766 has disclosed that the relationship of the odor and relative configuration of 2 and 3-positions that a mixture of anti-diastereomers is 500 times that of a syn-form diastereomer mixture, but has no mention of the relation between the absolute configuration of the 1-position of the trimethylcyclopentene ring and the odor.

(3) Regarding the four optical isomers and diastereomer mixtures of (E)-3,3-dimethyl-5-(2,2,3-trimethylcyclopent-3-en-1-yl)-4-penten-2-ol, U.S. Pat. No. 5,512,543 has described that the (1R)-isomer (mixture of diastereomers in which the 2-position is racemic) has a milky and strong sandalwood-like odor; the (1S)-isomer (mixture of diastereomers in which the 2-position is racemic) is drier than the (1R)-isomer and has a sandal cedar note; the (1S,2S)-isomer has a milky and strong sandalwood oil odor with a faint animal note; the (1S,2R)-isomer has a weak and flat sandalwood-like odor; the (1R,2S)-isomer has a more pleasant odor than the (1R,2R)-isomer and bears the odor of the (1R)-isomer (diastereomer mixture in which the 2-position is racemic); and a (2S)-isomer (mixture of diastereomers in which the 1-position is racemic) has a pleasant odor.

SUMMARY OF THE INVENTION

An object of the present invention is to provide an (E)-(R)-2-alkyl-4-(2,2,3-trimethylcyclopent-3-en-1-yl)-2-buten-1-ol which is different from known racemic mixtures and has an excellent odor and a perfume composition containing the same.

As a result of extensive study, the inventors of the present invention have found that an (E)-(R)-2-alkyl-4-(2,2,3-trimethylcyclopent-3-en-1-yl)-2-buten-1-ol can easily be obtained by hydrogenating an (E)-(R)-2-alkyl-4-(2,2,3-trimethylcyclopent-3-en-1-yl)-2-buten-1-al (hereinafter sometimes referred to as the (E-R) compound) in the presence of a base, an amine, and a ruthenium-phosphine complex catalyst. They have synthesized an (E)-(S)-2-alkyl-4-(2,2,3-trimethylcyclopent-3-en-1-yl)-2-buten-1-ol, which is an antipode of the (E-R)-compound, and have these optical isomers and their racemic mixture evaluated in terms of odor by specialized panelists. As a result, they found that the configuration of the 1-position of the cyclopentene ring is greatly influential on the odor.

That is, the novel (E)-(R)-2-alkyl-4-(2,2,3-trimethylcyclopent-3-en-1-yl)-2-buten-1-ol was found to have markedly excellent odor compared with its diastereomer or racemic mixture and to be very useful as a perfume material having a sandalwood oil odor. The present invention has been completed based on this finding.

The present invention provides an (E)-(R)-2-alkyl-4-(2,2,3-trimethylcyclopent-3-en-1-yl)-2-buten-1-ol represented by formula (I):

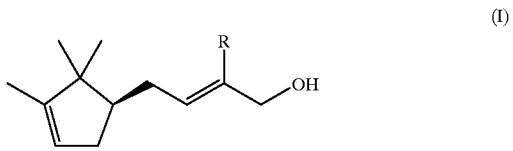

wherein R represents a straight-chain or branched alkyl group having 1 to 3 carbon atoms; a process for preparing the compound of formula (I) comprising hydrogenating an (E)-(R)-2-alkyl-4-(2,2,3-trimethylcyclopent-3-en-1-yl)-2-buten-1-al represented by formula (II):

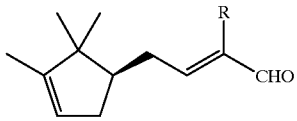

(II)

wherein R is as defined above, in the presence of a ruthenium-phosphine complex as a catalyst, a base comprising an alkali metal or an alkaline earth metal, and an amine; and a perfume composition containing the compound of formula (I).

DETAILED DESCRIPTION OF THE INVENTION

The alkyl group of the (E)-(R)-2-alkyl-4-(2,2,3-trimethylcyclopent-3-en-1-yl)-2-buten-1-ol of formula (I) includes a methyl group, an ethyl group, a propyl group, and an isopropyl group. (E)-(R)-2-Methyl-4-(2,2,3-trimethylcyclopent-3-en-1-yl)-2-buten-1-ol gives off a fresh sandalwood oil odor, and (E)-(R)-2-ethyl-4-(2,2,3-trimethylcyclopent-3-en-1-yl)-2-buten-1-ol has a strong, clean and bright odor. The latter compound is preferred.

The term "(E)-isomer" as used herein denotes a compound in which the trimethylcyclopentene ring and the formyl group or hydroxymethyl group are in a trans configuration.

The term "optically active" is used herein for a substance having an optical purity (enantiomer excess: % e.e.) of at least 50% e.e. The optical purity of an (R)-isomer is obtained by subtracting an (S)-isomer content (%) from an (R)-isomer content (%); and that of an (S)-isomer is calculated by subtracting an (R)-isomer content (%) from an (S)-isomer content (%).

A 2-alkyl-4-(2,2,3-trimethylcyclopent-3-en-1-yl)-2-buten-1-ol can be synthesized through known routes. The following process is known as one of them.

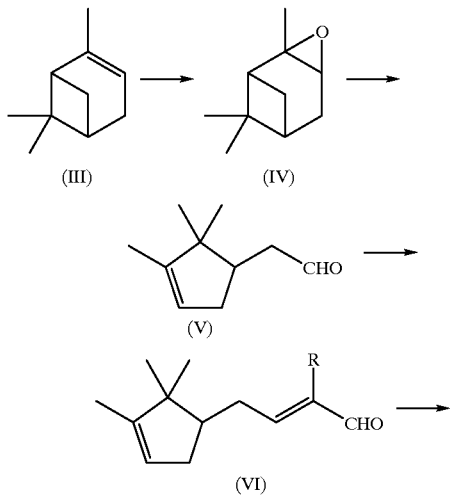

-continued

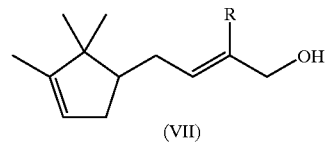

(VII)

wherein R is as defined above.

That is, commercially available α-pinene (III) is epoxidized, and the resulting α-pinene oxide (IV) is subjected to transformation reaction using a Lewis acid, such as zinc bromide, to obtain camphorenic aldehyde (V) (see J. B. Lewis, et al., *J. Org. Chem.*, Vol. 30, pp. 4271–4275 (1965)). An Aldol reaction between camphorenic aldehyde (V) and an aldehyde gives a 2-alkyl-4-(2,2,3-trimethylcyclopent-3-en-1-yl)-2-buten-1-al (VI) (see German Patent 68936). While the compound (VI) as obtained is usually a mixture of an (E)-isomer and a (Z)-isomer, when the alkyl group on the 2-position is as small as specified in the present invention, the steric hindrance is small so that a thermodynamically stable (E)-isomer is produced preferentially.

There have been many reports on the hydrogenation of the formyl compound (VI) into an (E)-2-alkyl-4-(2,2,3-trimethylcyclopent-3-en-1-yl)-2-buten-1-ol (VII), but the known hydrogenation techniques have their several disadvantages. For example, catalytic hydrogenation using a solid catalyst, such as a Raney nickel catalyst, a copper-chromium catalyst, and a Raney copper catalyst, has the disadvantage of being accompanied by hydrogenation of the double bond in competition with reduction of the aldehyde group, resulting in a low purity of the product. Chemical reduction using lithium aluminum hydride or sodium borohydride or Meerwein-Pondorf reduction using an aluminum alkoxide are superior in the regio-selectivity to an aldehyde group. However, the process of using lithium aluminum hydride is unsuitable for mass production because of the expensiveness and high danger of ignition of lithium aluminum hydride. The processes using sodium borohydride or an aluminum alkoxide require many steps for isolating a pure product, and the reagents used are expensive, too. Therefore, the yield attained is low, and the cost of production is high.

In contrast, the hydrogenation process according to the present invention which is carried out in the presence of a ruthenium-phosphine complex as a catalyst and a base comprising an alkali metal or an alkaline earth metal and an amine has the advantages of simple steps, inexpensive reagents, and reduction selectivity to the ketone moiety, providing the compound (I) in high yield.

The compound (II) which can be used in the present invention as a starting material is prepared from commercially available (1S,5S)-α-pinene having formula (VIII) in accordance with the above-described known process.

(VIII)

According to the process of the invention the compound (I) can be obtained by retention of the chirality of (1S,5S)-α-pinene (VIII). The optical purity of the compound (I) is dependent on that of the compound (II), and the optical purity of the compound (II) is dependent on that of (1S,5S)-

α-pinene. The inventors have experimentally confirmed that the optical purity of the compound (I) is in agreement with that of the α-pinene used as a starting material.

More specifically, the inventors synthesized (E)-(R)-2-ethyl-4-(2,2,3-trimethylcyclopent-3-en-1-yl)-2-buten-1-ol (IX) and (E)-(S)-2-ethyl-4-(2,2,3-trimethylcyclopent-3-en-1-yl)-2-buten-1-ol (XI) from (1S,5S)-α-pinene and (1R,5R)-α-pinene, respectively. The resulting compounds (IX) and (XI) were esterified with (R)-2-methoxy-2-phenyl-3,3,3-trifluoropropionic acid (hereinafter abbreviated as MTPA) to obtain esters of the respective diastereomers.

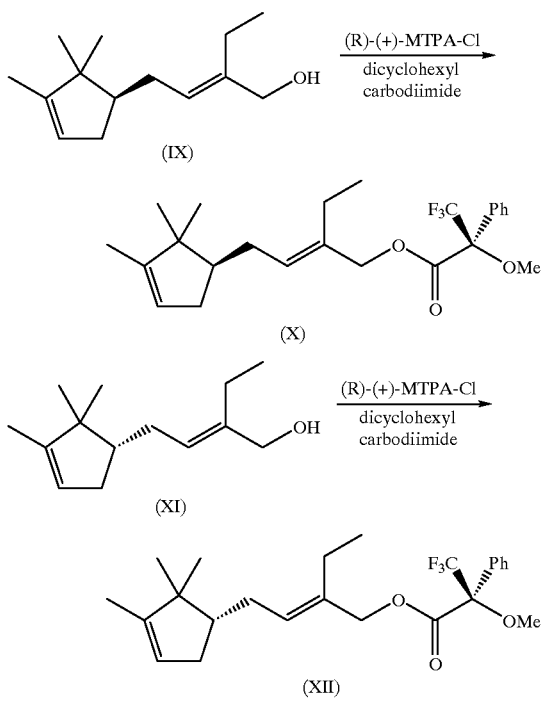

The ¹H-NMR spectrum of a mixture of the (R)-(R)-diastereomer (X) and the (S)-(R)-diastereomer (XII) exhibits 8 peaks in two sets of a quartet having different coupling constants assigned to the methylene group on 1-position. Each of the compounds (X) and (XII) obtained by the process of the invention shows only 4 peaks, proving to be a single diastereomer. It has now been confirmed that the stereoisomerism of the starting α-pinene remains in the final product.

Accordingly, in order to obtain the compound (I) having an optical purity of 50% e.e. or higher, the starting (1S,5S)-α-pinene should have an optical purity of 50% e.e. or higher.

Synthesis of the compound (II) from (1S,5S)-α-pinene according to a known process is accompanied with by-production of a small amount of a (Z)-(R)-2-alkyl-4-(2,2,3-trimethylcyclopent-3-en-1-yl)-2-buten-1-al (XIII). The compound (II) is led to the compound (I) by hydrogenation, while the compound (XIII) is led to a corresponding (Z)-(R)-2-alkyl-4-(2,2,3-trimethylcyclopent-3-en-1-yl)-2-buten-1-ol (XIV) as illustrated below. In other words, the process of the present invention guarantees that all stereocenters are retained throughout the reactions involved.

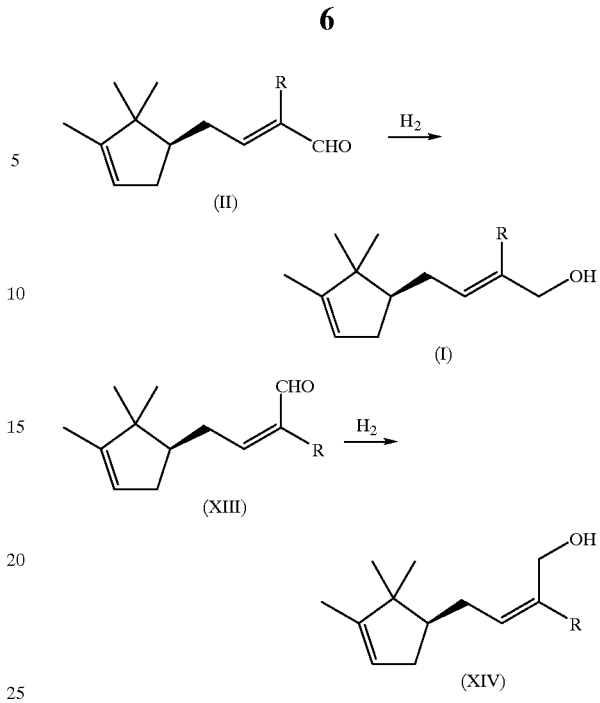

wherein R is as defined above.

As mentioned above, when the process of the invention is followed, there is obtained a mixture consisting of the compound (I) ((E-R)-compound) and a small proportion of the (Z)-(R)-compound (XIV). The inventors have isolated each compound from the mixture and determined their structures by two-dimensional NMR.

The (E)-(R)-2-alkyl-4-(2,2,3-trimethylcyclopent-3-en-1-yl)-2-buten-1-ol (I) was synthesized for the first time by the inventors.

The ruthenium-phosphine complex which is used as a catalyst for hydrogenating the compound (II) is a compound composed of ruthenium with a phosphine compound, preferably an organic phosphine compound, coordinated as a ligand. The complex may have an auxiliary ligand. it may be either a mononuclear complex or a polynuclear complex.

Commercially available ruthenium-phosphine complexes can be utilized as such, or a complex may be prepared on use. The complex can be prepared by adding 1 to 4 equivalents of a ligand compound to ruthenium. Alternatively, the complex may be prepared in situ by separately adding a ruthenium salt or a ruthenium complex and a ligand to the hydrogenation reaction system. Complexes having the ligand in excess, those to which triethylamine or a Lewis acid has been added, or those activated by reduction may also be used.

The organic phosphine compound coordinating to ruthenium may be either monodentate or polydentate. Monodentate ligands include those represented by formula (XV):

$$PR^1R^2R^3 \qquad (XV)$$

wherein $R^1$, $R^2$, and $R^3$, which may be the same or different, each represent a substituted or unsubstituted alkyl group, a substituted or unsubstituted aralkyl group or a substituted or unsubstituted aryl group; and bidentate ligands include those represented by formula (XVI):

$$R^4R^5P{-}A^1{-}PR^6R^7 \qquad (XVI)$$

wherein $R^4$, $R^5$, $R^6$, and $R^7$, which may be the same or different, each represent a substituted or unsubstituted alkyl group, a substituted or unsubstituted aralkyl group or a substituted or unsubstituted aryl group; and $A^1$ represents a substituted or unsubstituted alkylene group, $-A^2-Ar-Ar-A^2-$ or $-Ar-Ar-$, wherein $A^2$ represents a substituted or unsubstituted alkylene group; and $-Ar-Ar-$ represents a 1,1'-biphenylene group having a bond at the 2,2'-positions, a 1,1'-binaphthylene group having a bond at the 2,2'-positions, or 5,5',6,6',7,7',8,8'-octahydro-1,1'-binaphthylene group having a bond at the 2,2'-positions, in which the biphenylene group may be substituted with a methyl group, a methoxy group or a dialkylamino group, and the binaphthylene group may be substituted with an alkali sulfonate group.

The substituted or unsubstituted alkyl group as represented by $R^1$, $R^2$, $R^3$, $R^4$, $R^5$, $R^6$ or $R^7$ includes a straight-chain, branched or cyclic alkyl group which may have one or more substituents, such as a halogen atom and an alkoxy group, preferably a straight-chain or branched alkyl group having 1 to 10 carbon atoms and a cyclic alkyl group having 3 to 8 carbon atoms. Specific examples of the alkyl group are methyl, ethyl, butyl, octyl, and cyclohexyl groups.

The substituted or unsubstituted aralkyl group as represented by $R^1$, $R^2$, $R^3$, $R^4$, $R^5$, $R^6$ or $R^7$ includes an alkyl group (preferably an alkyl group having 1 to 4 carbon atoms) substituted by an aryl group (preferably a phenyl group or a naphthyl group) which may have one or more substituents, such as a halogen atom, an alkyl group, and an alkoxy group. Specific examples of the aralkyl group are benzyl, phenethyl and naphthylmethyl groups.

The substituted or unsubstituted aryl group as represented by $R^1$, $R^2$, $R^3$, $R^4$, $R^5$, $R^6$ or $R^7$ includes an aryl group which may have one or more substituents, such as a halogen atom, an alkyl group, and an alkoxy group, preferably a phenyl or naphthyl group which may be substituted with a chlorine atom, a bromine atom, an iodine atom, a fluorine atom, a straight-chain or branched alkyl group having 1 to 4 carbon atoms or a straight-chain or branched alkoxy group having 1 to 4 carbon atoms. Specific examples of the aryl group include phenyl, naphthyl, p-chlorophenyl, p-bromophenyl, p-fluorophenyl, p-tolyl, p-t-butylphenyl, 3,5-dimethylphenyl, and p-methoxyphenyl groups, with phenyl and p-tolyl groups being particularly preferred.

The substituted or unsubstituted alkylene group as represented by $A^1$ or $A^2$ denotes a straight-chain or branched alkylene group which may have one or more substituents, such as a halogen atom and an alkoxy group, preferably an unsubstituted straight-chain or branched alkylene group having 1 to 5 carbon atoms. Specific examples of $A^1$ are an ethylene group (—(CH$_2$)$_2$—), a trimethylene group (or 1,3-propylene group) (—(CH$_2$)$_3$—), a tetramethylene group (or 1,4-butylene group) (—(CH$_2$)$_4$—), and a dimethylethylene group (or 2,3-butylene group) (—CH(CH$_3$)CH(CH$_3$)—). Specific examples of $A^2$ include a methylene group (—CH$_2$—).

Examples of preferred ligands represented by formula (XV) are trimethylphosphine, triethylphosphine, tributylphosphine, trioctylphosphine, tricyclohexylphosphine, tribenzylphosphine, triphenylphosphine, tri(p-chlorophenyl)phosphine, tri(p-bromophenyl)phosphine, tri(p-fluorophenyl)phosphine, tri(p-tolyl)phosphine, tri(p-t-butylphenyl)phosphine, tri(3,5-dimethylphenyl)phosphine, tri(p-methoxyphenyl)phosphine, methyldiphenylphosphine, and dimethylphenylphosphine.

Of the ligands represented by formula (XVI), those in which $A^1$ is a substituted or unsubstituted alkylene group preferably include 1,2-bis(dimethylphosphino)ethylene, 1,3-bis(dimethylphosphino)propylene, 1,4-bis(dimethylphosphino)butylene, 1,2-bis(dipehnylphosphino)ethylene (hereinafter abbreviated as DPPE), 1,3-bis(diphenylphosphino)propylene (hereinafter abbreviated as DPPP), 1,4-bis(diphenylphosphino)butylene (hereinafter abbreviated as DPPB), 1,2-bis[di(p-tolyl)phosphino]ethylene, 1,3-bis[di(p-tolyl)phosphino]propylene, 1,4-bis[di(p-tolyl)phosphino]butylene, and 2,3-bis(diphenylphosphino)butylene (hereinafter referred to as CHIRAPHOS).

Of the ligands represented by formula (XVI), those in which $A^1$ is $-A^2-Ar-Ar-A^2-$ preferably include 2,2'-bis(diphenylphosphinomethyl)-1,1'-biphenyl and 2,2'-bis(diphenylphosphinomethyl)-1,1'-binaphthyl.

Of the ligands represented by formula (XVI), those in which $A^1$ is $-Ar-Ar-$ preferably include 2,2'-bis(dicyclohexylphosphino)-6,6'-dimethyl-1,1'-biphenyl (hereinafter referred to as BICHEP), 6,6'-bis(diphenylphosphino)-2,2'-dimethyl-1,1'-biphenyl (hereinafter referred to as BIPHEMP), 6,6'-bis(diphenylphosphino)-2,2'-dimethoxy-1,1'-biphenyl, 2,2',4,4'-tetramethoxy-6,6'-bis(diphenylphosphino)-1,1'-biphenyl, 4,4'-bis(dimethylamino)-6,6'-bis(diphenylphosphino)-2,2'-dimethyl-1,1'-biphenyl, 2,2'-bis(diphenylphosphino)-1,1'-binaphthyl (hereinafter referred to as BINAP), 2,2'-bis(di-p-tolylphosphino)-1,1'-binaphthyl (hereinafter referred to as Tol-BINAP), 2,2'-bis(di-m-tolylphosphino)-1,1'-binaphthyl (hereinafter referred to as m-Tol-BINAP), 2,2'-bis(di-p-t-butylphenylphosphino)-1,1'-binaphthyl (hereinafter referred to as t-Bu-BINAP), 2,2'-bis[di-(3,5-dimethylphenyl)phosphino]-1,1'-binaphthyl (hereinafter referred to as DM-BINAP), 2,2'-bis-(di-p-methoxyphenylphosphino)-1,1'-binaphthyl (hereinafter referred to as MeO-BINAP), 2,2'-bis(di-p-chlorophenylphosphino)-1,1'-binaphthyl (hereinafter referred to as Cl-BINAP), 2,2'-bis(dicyclopentylphosphino)-1,1-binaphthyl (hereinafter referred to as CpBINAP), 2,2'-bis(dicyclohexylphosphino)-1,1'-binaphthyl (hereinafter referred to as CyBINAP), and 2,2'-bis(diphenylphosphino)-5,5',6,6',7,7',8,8'-octahydro-1,1'-binaphthyl (hereinafter referred to as $H_8$-BINAP).

Of the above-enumerated ligands represented by formula (XVI), CHIRAPHOS and those in which $A^1$ is $-A^2-Ar-Ar-A^2-$ or $-Ar-Ar-$ have an asymmetric center to produce an (S)-isomer, an (R)-isomer, or a racemate, any of which can be used in the present invention. In what follows, the indication of "(S)-" or "(R)-" for the ligands having an asymmetric structure is omitted in some cases.

Of the above-described ligands, particularly preferred in the practice of the present invention are those represented by formula (XVI).

The auxiliary ligands which may be used in the ruthenium-phosphine complex include 1,5-cyclooctadiene, norbornadiene, benzene, p-cymene, mesitylene, acetonitrile, benzonitrile, pyridine, quinoline, isoquinoline, acetic acid, and acetylacetonato.

Complexes 1 to 4 represented by the following formulae (XVII) to (XX) are examples of preferred ruthenium-phosphine complexes.

Complex 1: $RuH_a(X^1)_bL_c$     (XVII)

wherein $X^1$ represents a halogen atom or $R^8COO$, wherein $R^8$ represents a hydrogen atom, a lower alkyl group having 1 to 4 carbon atoms or a lower haloalkyl group having 1 to 4 carbon atoms; L represents an organic phosphine compound; a and b each represent an integer of 0 to 2, giving the sum of 2; and c represents an integer of 1 to 4.

Complex 2: $(RuH_dL_e)(X^2)_f$     (XVIII)

wherein $X^2$ represents $ClO_4$, $PF_6$ or $BF_4$; L is as defined above; where L is a monodentate ligand, e is 2, and f is 2 when d is 0, or e is 4, and f is 1 when d is 1; and where L is a bidentate ligand, e is 1, and f is 2 when d is 0, or e is 2, and f is 1 when d is 1.

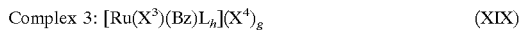
Complex 3: $[Ru(X^3)(Bz)L_h](X^4)_g$ (XIX)

wherein $X^3$ represents a halogen atom; Bz represents a substituted or unsubstituted benzene ring; $X^4$ represents a halogen atom, $ClO_4$, $PF_6$, $BF_4$ or $BPh_4$ (wherein Ph stands for a phenyl group, hereinafter the same); L is as defined above; g represents 1 or, where $X^3$ and $X^4$ are each an iodine atom, g may be 3; and h represents 2 where L is a monodentate ligand, or h represents 1 where L is a bidentate ligand.

Complex 4: $(Ru_2Cl_4L_w)(T)$ (XX)

wherein T represents a tertiary amine; L is as defined above; and w is 4 where L is a monodentate ligand, or w is 2 where L is a bidentate ligand.

In formulae (XVII) to (XX), the organic phosphine compound as L is selected from those enumerated above.

In formula (XVII), $X^1$ preferably represents a chlorine atom, a bromine atom, an iodine atom, HCOO, $CH_3COO$, and $CF_3COO$, with a chlorine atom being particularly preferred. The integers a and b make three combinations; (a=0, b=2), (a=1, b=1), and (a=2, b=0). The combination (a=0, b=2) is preferred. Where $X^1$ is a halogen atom, c is preferably 3 or 4.

In formula (XIX), the halogen atom as $X^3$ or $X^4$ includes a chlorine atom, a bromine atom, and an iodine atom. The substituted or unsubstituted benzene ring as Bz means a benzene ring which may have one or more substituents selected from an alkyl group, an alkoxy group, an alkoxycarbonyl group, a halogen atom, etc. Preferred examples of Bz include unsubstituted benzene and benzene substituted with an alkyl group having 1 to 4 carbon atoms, an alkoxy group having 1 to 4 carbon atoms, an alkoxycarbonyl group having 1 to 4 carbon atoms, a chlorine atom, a bromine atom, or an iodine atom. Specific examples are benzene, toluene, xylene, trimethylbenzene, hexamethylbenzene, ethylbenzene, t-butylbenzene, p-cymene, cumene, anisole, methyl benzoate, and chlorobenzene.

In the formula (XX), the tertiary amine as T includes triethylamine, tributylamine, ethyldiisopropylamine, 1,8-bis(dimethylamino)naphthalene, dimethylaniline, pyridine, and N-methylpiperidine, with triethylamine being preferred.

Preferred examples of complexes 1 to 4 are shown below.
Complex 1:
$RuH_2(PPh_3)_4$
$RuHCl(PPh_3)_3$
$RuH(HCOO)(PPh_3)_3$
$RuH(CH_3COO)(PPh_3)_3$
$RuCl_2(PPh_3)_3$
$RuBr_2(PPh_3)_3$
$RuI_2(PPh_3)_3$
$RuCl_2[P(CH_3)Ph_2]_4$
$RuCl_2[P(CH_3)_2Ph]_4$
$RuCl_2[P(CH_3)_3]_4$
$RuCl_2[Ph_2P-(CH_2)_2-PPh_2]_2$
$RuCl_2(CHIRAPHOS)_2$
$RuCl_2(BINAP)$
$Ru(CH_3COO)_2(Tol-BINAP)$
$Ru(CF_3COO)_2(Tol-BINAP)$
Complex 2:
$[Ru(BINAP)](ClO_4)_2$
$[Ru(m-Tol-BINAP)](PF_6)_2$
$[Ru(MeO-BINAP)](BF_4)_2$
$[RuH(BIPHEMP)_2]ClO_4$
$[RuH(t-Bu-BINAP)_2]PF_6$
Complex 3:
$[RuCl(benzene)(BINAP)]Cl$
$[RuCl(p-cymene)(DPPE)]Cl$
$[RuCl(p-cymene)(DPPP)]Cl$
$[RuCl(p-cymene)(DPPB)]Cl$
$[RuI(benzene)(Tol-BINAP)]I$
$[RuI(p-cymene)(Tol-BINAP)]I$
$[RuI(p-cymene)(BINAP)]I_3$
Complex 4:
$[Ru_2Cl_4(BINAP)_2](NEt_3)$ (Et stands for an ethyl group, hereinafter the same)
$[Ru_2Cl_4(DM-BINAP)_2](NEt_3)$
$[Ru_2Cl_4(H_8-BINAP)_2](NEt_3)$ Complexes 1 are particularly preferred among complexes 1 to 4 in view of their reaction selectivity.

The base comprising an alkali metal or an alkaline earth metal which can be used in the present invention may be either organic or inorganic, including compounds represented by formula (XXI):

$$M(R^9) \tag{XXI}$$

wherein M represents an alkali metal or an alkaline earth metal, preferably an alkali metal; and $R^9$ represents a hydroxyl group, an alkoxy group having 1 to 4 carbon atoms, or a mercapto group.

Preferred examples of the base (XXI) are KOH, $Ca(OH)_2$, KOMe, KOt-Bu, LiOH, LiOMe, LiOt-Bu, NaOH, NaOMe, and $Mg(OMe)_2$ (wherein Me stands for a methyl group, and t-Bu a t-butyl group, hereinafter the same), with those having an alkali metal being still preferred. KOH and NaOH are particularly preferred.

The base is preferably used in an amount of about 0.5 to 100 equivalents, particularly about 1 to 40 equivalents, to the complex.

The amine which can be used in the present invention includes primary, secondary or tertiary amines represented by formula (XXII):

$$NR^{10}R^{11}R^{12} \tag{XXII}$$

wherein $R^{10}$, $R^{11}$, and $R^{12}$, which may be the same or different, each represent a hydrogen atom; a substituted or unsubstituted alkyl group, a substituted or unsubstituted aralkyl group or a substituted or unsubstituted aryl group; provided that $R^{10}$, $R^{11}$, and $R^{12}$ do not simultaneously represent a hydrogen atom; primary, secondary or tertiary diamines represented by formula (XXIII):

$$NR^{13}R^{14}-Z-NR^{15}R^{16} \tag{XXIII}$$

wherein $R^{13}$, $R^{14}$, $R^{15}$, and $R^{16}$, which may be the same or different, each represent a hydrogen atom, a substituted or unsubstituted alkyl group, a substituted or unsubstituted aralkyl group or a substituted or unsubstituted aryl group; and Z represents a substituted or unsubstituted and saturated or unsaturated hydrocarbon chain having 1 to 6 carbon atoms or a substituted or unsubstituted and saturated or unsaturated hydrocarbon ring having 3 to 6 carbon atoms; and cyclic amines.

The substituted or unsubstituted alkyl group as $R^{10}$, $R^{11}$, $R^{12}$, $R^{13}$, $R^{14}$, $R^{15}$, and $R^{16}$ includes straight-chain, branched or cyclic alkyl groups which may have one or more substituents, such as an alkoxy group. Straight-chain or branched alkyl groups having 1 to 10 carbon atoms and cycloalkyl groups having 5 to 8 carbon atoms are still preferred.

The substituted or unsubstituted aralkyl group as $R^{10}$, $R^{11}$, $R^{12}$, $R^{13}$, $R^{14}$, $R^{15}$, and $R^{16}$ includes an alkyl group substituted with an aryl group that may have one or more substituents, such as an alkyl group and an alkoxy group. The aryl moiety in the aralkyl group is preferably a substituted or unsubstituted phenyl group, and the alkyl moiety preferably has 1 to 4 carbon atoms. A benzyl group is an example.

The substituted or unsubstituted aryl group as $R^{10}$, $R^{11}$, $R^{12}$, $R^{13}$, $R^{14}$, $R^{15}$, and $R^{16}$ includes an aryl group which may have one or more substituents, such as an alkyl group and an alkoxy group. Preferred examples include a phenyl or naphthyl group which may be substituted with a straight-chain or branched alkyl group having 1 to 4 carbon atoms or a straight-chain or branched alkoxy group having 1 to 4 carbon atoms.

Specific examples of the amines include monoamines, such as methylamine, ethylamine, propylamine, isopropylamine, butylamine, isobutylamine, t-butylamine, hexylamine, octylamine, dodecylamine, cyclopentylamine, cyclohexylamine, benzylamine, dimethylamine, diethylamine, dipropylamine, diisopropylamine, dibutylamine, diisobutylamine, di-t-butylamine, dihexylamine, dicyclopentylamine, dicyclohexylamine, dibenzylamine, trimethylamine, triethylamine, tripropylamine, ethyldiisopropylamine, tributylamine, trihexylamine, tribenzylamine, benzyldimethylamine, aniline, p-toluidine, N,N-dimethylaniline, diphenylamine, triphenylamine, piperidine, piperazine, morpholine, N-methylpiperidine, N-methylpiperazine, and N-methylmorpholine; diamines, such as ethylenediamine, trimethylenediamine, tetramethylenediamine, pentamethylenediamine, hexamethylenediamine, N-methylethylenediamine, N,N'-dimethylethylenediamine, N,N'-dimethylpropylenediamine, N,N'-dimethyltetramethylenediamine, N,N'-diethylethylenediamine, N,N'-diethylpropylenediamine, N,N'-diethyltetramethylenediamine, N,N'-dibenzylethylenediamine, N,N'-dibenzylpropylenediamine, N,N'-dibenzyltetramethylenediamine, N,N'-diphenylethylenediamine, N,N-diphenylpropylenediamine, N,N'-diphenyltetramethylenediamine, N,N,N'-trimethylethylenediamine, tetramethylethylenediamine, tetramethylpropylenediamine, tetramethyltetramethylenediamine, tetraethylethylenediamine, tetraethylpropylenediamine, tetraethyltetramethylenediamine, tetrabenzylethylenediamine, tetrabenzylpropylenediamine, tetrabenzyltetramethylenediamine, tetraphenylethylenediamine, tetraphenylpropylenediamine, tetraphenyltetramethylenediamine, and o-phenylenediamine; and optically active diamines, such as optically active 1,2-diphenylethylenediamine, optically active 1,3-diphenylpropylenediamine, optically active 1,4-diphenyltetramethylenediamine, optically active 1,2-diaminopropane, optically active 1,1-diphenyl-1,2-diaminopropane, optically active 1,1-di(p-methoxyphenyl)-1,2-diaminopropane, optically active 2,3-diaminobutane, optically active 2,4-diaminopentane, optically active 2,5-diaminohexane, optically active 1,2-diaminocyclopentane, and optically active 1,2-diaminocyclohexane.

Of these amines preferred are diamines represented by formula (XXIII). Particularly preferred are primary diamines (XXIII) in which $R^{13}$, $R^{14}$, $R^{15}$, and $R^{16}$ all represent a hydrogen atom, and Z is saturated hydrocarbon chain having 1 to 4 carbon atoms, such as ethylenediamine, trimethylenediamine, and tetramethylenediamine.

The monoamine is used in an amount of about 1 to 8 equivalents, preferably about 2 to 4 equivalents, to the complex, and the diamine is used in an amount of about 0.5 to 4 equivalents, preferably about 1 to 4 equivalents, to the complex.

The process of the present invention is carried out by hydrogenating the compound (II) in the presence of the base and the amine using the ruthenium-phosphine complex as a catalyst in a hydrogen atmosphere. The catalyst is used in an amount of about 1/5 to 1/100000 mol, preferably about 1/200 to 1/50000 mol, per mole of the substrate, i.e., the compound (II) (substrate/catalyst molar ratio=about 5 to 100000, preferably about 200 to 50000). The reaction is preferably conducted with stirring. In particular, when the reaction is carried out with a small amount of the catalyst, it is preferable to mechanically stir the reaction system by means of a mechanical stirrer, etc.

The reaction temperature ranges usually from about −300 to 250° C., preferably from about −10° to 100° C. Within this range, a low temperature is preferred from the standpoint of reaction selectivity, and a high temperature is preferred for obtaining an increased reaction rate.

The reaction usually completes in several minutes to about 30 hours while varying depending on the concentration of the reaction substrate, the amount of the catalyst, the temperature, the hydrogen pressure, and the like. The completion of the reaction is confirmed by gas chromatography, etc.

The hydrogen pressure is preferably about 1 to 200 atm., still preferably about 3 to 100 atm. Hydrogen gas can be used as diluted with an inert gas, such as methane, nitrogen, argon, helium, carbon dioxide, etc., either alone or as a mixture thereof.

The reaction can be performed with or without a solvent. Any solvent may be used with no particular limitation as long as it gives no adverse influence on the reaction. Examples of suitable solvents include water; hydrocarbons, such as hexane, heptane, octane, nonane, decane, benzene, toluene, and xylene; ethers, such as tetrahydrofuran, dioxane, dimethoxyethane, diisopropyl ether, and diethylene glycol dimethyl ether; esters, such as ethyl acetate, butyl acetate, ethyl propionate, and ethyl acetoacetate; alcohols, such as methanol, ethanol, n-propanol, and isopropyl alcohol; nitriles, such as acetonitrile; phosphorous acid and esters thereof, such as phosphorous acid, trimethyl phosphite, dimethyl phosphite, monomethyl phosphite, triethyl phosphite, tributyl phosphite, trioctyl phosphite, triphenyl phosphite, dimethylphenyl phosphite, and methyldiphenyl phosphite; sulfoxides, such as dimethyl sulfoxide, diethyl sulfoxide, dibenzyl sulfoxide, diphenyl sulfoxide, and tetramethylene sulfoxide; and amides, such as formamide, N,N-dimethylformamide, N,N-dimethylacetamide, and N-methylpyrrolidone. These solvents can be used either individually or as a combination of two or more thereof. Of these solvents preferred are alcohols, such as methanol, ethanol, and isopropyl alcohol. Isopropyl alcohol is a particularly preferred solvent.

While the amount of the solvent, if used, is not particularly limited, it is preferably about 0.5 to 100 times the weight of the reaction substrate.

After completion of the reaction, the reaction mixture is purified in a conventional manner by, for example, filtration, concentration under reduced pressure, distillation, and the like.

The threshold value of the odor of the compound (I) was determined by a triangle method well-known in the art (see T. E. Acree, et al., *J. Argric. Food Chem.*, Vol. 33, pp. 425–427 (1985)). It was revealed as a result that the threshold value of (E)-(R)-2-ethyl-4-(2,2,3-trimethylcyclopent-3-en-1-yl)-2-buten-1-ol (IX) is 1/40 of that of its enantiomer, i.e., (E)-(S)-2-ethyl-4-(2,2,3-trimethylcyclopent-3-en-1-yl)-2-buten-1-ol (XI) and that the threshold value of (E)-(R)-2-methyl-4-(2,2,3-trimethylcyclopent-3-en-1-yl)-2-buten-1-ol (XXIV) is 1/8 of that of its enantiomer, i.e., (E)-(S)-2-methyl-4-(2,2,3-trimethylcyclopent-3-en-1-yl)-2-buten-1-ol (XXV). In other words, the odor of the (E-R)-ethyl compound (IX) is about 40 times as strong as the (E-S)-ethyl compound (XI), and the odor of the (E-R)-methyl compound (XXIV) is about 8 times as strong as its enantiomer (XXV).

The (E-R)-ethyl compound (IX) has a clean and warm sandalwood oil odor, while the (Z-R)-ethyl compound (XXVI) is inferior in strength of odor to the compound (IX), and its odor has butter-like sweetness, lacking a woody note. Thus, the (E-R)-ethyl compound (IX) has an excellent sandalwood oil odor, and responsible for the odor characteristic of the compound according to the present invention.

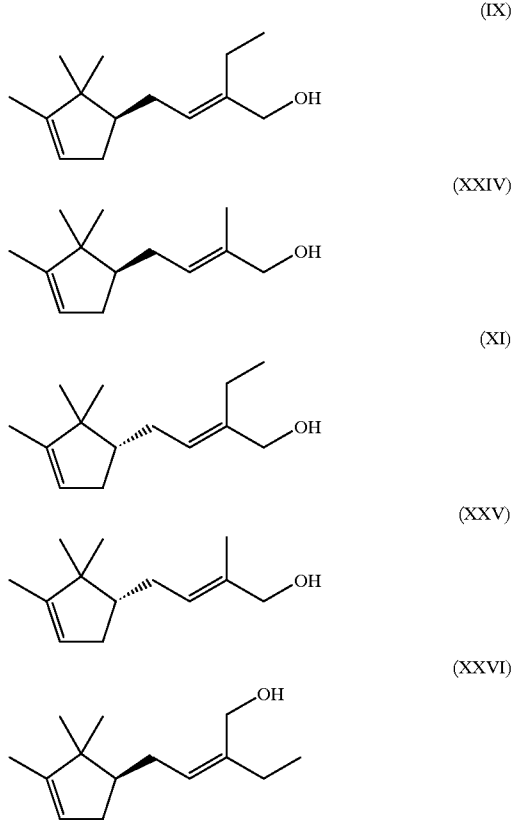

(IX)

(XXIV)

(XI)

(XXV)

(XXVI)

In carrying out the present invention, the starting (1S,5S)-α-pinene does not always need to be optically pure. The inventors prepared an (E)-(R)-2-alkyl-4-(2,2,3-trimethylcyclopent-3-en-1-yl)-2-buten-1-ol having an optical purity of about 50% e.e. starting from (1S,5S)-α-pinene having an optical purity of about 50% e.e. that is available with relative ease. Substantially indistinguishable in odor from a substantially optically pure compound, the resulting compound achieves the object of the present invention and is economically more advantageous.

It has been thus confirmed that the compound (I) has an excellent sandalwood oil odor that is more pleasant and stronger than the odor of its enantiomer, (E)-(S)-2-alkyl-4-(2,2,3-trimethylcyclopent-3-en-1-yl)-2-buten-1-ol, or a racemic mixture of the compound (I) and its enantiomer.

Blending the compound (I) provides perfume compositions having a fresh and appealing sandalwood oil odor and serving as an odorant, a modifier, an intensifier, and the like. The content of the compound (I) in the perfume composition of the invention is not particularly limited and is decided appropriately in accordance with the purpose. For example, the compound (I) is usually used in an amount of about 0.1 to 50% by weight based on the total composition. If desired, the perfume composition can contain compounded perfumes or bases for compounding commonly employed in the art.

The perfume composition of the invention is useful in various cosmetics, fragrances, toiletries, and the like. More specifically, the perfume composition is added to toiletries, such as soaps, shampoos, rinses, tooth pastes, and mouth washes; hair care cosmetics, such as hair dyes and hair tonics; cosmetics for foundation, such as creams, lotions, and face packs; cosmetics for make-up, such as face powder, foundation, and rouge; fragrances, such as perfumes and eau-de-cologne; suntan lotions or sunscreens; lip cosmetics, such as lip sticks and lip creams; deodorants and room odorant; hygienic goods, such as disinfectants and insecticides; bleach, softeners, dishwashing detergents, and so on, in an appropriate amount for adding its odor to thereby increase their commercial value.

As described above, the present invention provides a novel optically active compound, (E)-(R)-2-alkyl-4-(2,2,3-trimethylcyclopent-3-en-1-yl)-2-buten-1-ol, in high yield with ease. This compound has a strong and excellent sandalwood oil odor clearly distinguishable from the odor of conventional synthetic compounds, and the perfume compositions containing the same are effectively used in wide fields including cosmetics, fragrances, toiletries, and hygienic goods.

The present invention will now be illustrated in greater detail with respect to Examples, but it should be understood that the present invention is not construed as being limited thereto.

In Examples, various analyses were made with the following instruments.

Gas Chromatography (GC):

Gas chromatograph: HP-5890, manufactured by Hewlett Packard

Column: PEG BC-WAX (0.25 mm×50 mm), manufactured by GL-Science K.K.

Measuring temperature: 100 to 220° C. (increased at a rate of 10° C./min)

Injection temperature: 250° C.

Retention time:

(1) (E)-(R)-2-Alkyl-4-(2,2,3-trimethylcyclopent-3-en-1-yl)-2-buten-1-ol: about 12.7 min (area intensity: $a_1$)

(2) Other isomers: about 11.2 to 12.4 min (area intensity: $a_2$)

(3) (E)-(R)-2-Alkyl-4-(2,2,3-trimethylcyclopent-3-en-1-yl)-2-buten-1-al: about 10.3 min (area intensity: $a_3$)

(4) (E)-(S)-2-Alkyl-4-(2,2,3-trimethylcyclopent-3-en-1-yl)-2-buten-1-al: about 9.4 min (area intensity: $a_4$)

Conversion (%): $[(a_1+a_2)/(a_1+a_2+a_3+a_4)]\times 100$

Reaction selectivity (%): $[a_1/(a_1+a_2)]\times 100$

Preparative High-Performance Liquid Chromatography (HPLC):
   Chromatograph: PU-615, manufactured by GL-Science K.K.
   Column: INERTSIL ODS-3 (20×250 mm), manufactured by Nakarai Tesc K.K.
   Solvent: methanol
   Flow rate: 10 ml/min
   Detector: RI-98 (refractive index: preparative), manufactured by Labo System
Infrared Absorption Spectrum (IR):
   IR spectrophotometer: IR-810, JASCO Inc.
   Measuring method: liquid film method
Mass Spectrum (MS):
   Mass spectrometer: M-80B (ionization voltage: 20 eV), manufactured by Hitachi, Ltd.
Proton Nuclear Magnetic Resonance ($^1$H-NMR):
   NMR spectrometer: AM-400 (400 MHz), manufactured by Bruker, Inc.
   Internal standard: tetramethylsilane
Specific Rotation:
   Polarimeter: DIP-370, manufactured by JASCO Inc.

EXAMPLE 1

Synthesis of (E)-(R)-2-Methyl-4-(2,2,3-trimethylcyclopent-3-en-1-yl)-2-butene-1-ol In a 100 ml stainless steel autoclave were charged 3.84 g (0.02 mol) of (E)-(R)-2-methyl-4-(2,2,3-trimethylcyclopent-3-en-1-yl)-2-buten-1-al synthesized from (1S,5S)-α-pinene having an optical purity of 97% e.e. (available from Aldrich) in a conventional manner, 38.4 mg (0.04 mmol) of RuCl$_2$(PPh$_3$)$_3$, 4 ml of a 0.02M 1,3-diaminopropane (0.08 mmol) solution in isopropyl alcohol, and 12 ml of a 0.1M potassium hydroxide (1.2 mmol) solution in isopropyl alcohol in a nitrogen atmosphere, and the mixture was stirred at 0° C. for 3 hours under a hydrogen pressure of 50 atm.

The analysis of the reaction mixture by GC revealed that the conversion was 100% and the reaction selectivity was 98%. The reaction mixture was filtered, and the filtrate was concentrated under reduced pressure. The residue was dissolved in hexane, washed with a saturated sodium chloride aqueous solution, dried over anhydrous magnesium sulfate, and concentrated under reduced pressure. The resulting oily substance was distilled under reduced pressure to give 3.13 g (81%) of the title compound. The chemical purity of the product was found to be 98% by GC.

Boiling point: 125.7 to 126° C. (5 mmHg); Specific rotation: $a_D^{25}$=+0.71° MS (m/z): 194(M$^+$), 179, 161, 135, 121, 109, 95, 81, 67; IR (film) (cm$^{-1}$): 3325, 2950, 1460, 1440, 1360, 1015 $^1$H-NMR (CDl$_3$, δ ppm): 5.44 (1H, t, J=7.4 Hz), 5.22 (1H, brs), 4.01 (2H, brs), 2.28–1.99 (3H, m), 1.84–1.74 (2H, m), 1.69 (3H, s), 1.60 (3H, s), 1.45 (1H, s), 0.99 (3H, s), 0.80 (3H, s)

REFERENCE EXAMPLE 1

Synthesis of (E)-(S)-2-Methyl-4-(2,2,3-trimethylcyclopent-3-en-1-yl)-2-buten-1-ol (E)-(S)-2-Methyl-4-(2,2,3-trimethylcyclopent-3-en-1-yl)-2-buten-1-al synthesized from (1R,5R)-α-pinene having an optical purity of 97% e.e. (available from Aldrich) was hydrogenated in the same manner as in Example 1 to obtain 3.08 g (yield 80%) of the title compound. The chemical purity of the product was found to be 98% by GC.

Specific rotation: $\alpha_D^{25}$=−0.71°

The boiling point, MS, IR, and $^1$H-NMR data of the product were the same as those of Example 1.

EXAMPLE 2

Synthesis of (E)-(R)-2-Ethyl-4-(2,2,3-trimethylcyclopent-3-en-1-yl)-2-buten-1-ol In a 100 ml stainless steel autoclave were charged 4.12 g (0.02 mol) of (E)-(R)-2-ethyl-4-(2,2,3-trimethylcyclopent-3-en-1-yl)-2-buten-1-al synthesized from (1S,5S)-α-pinene having an optical purity of 97% e.e. in a conventional manner, 38.4 mg (0.04 mmol) of RuCl$_2$(PPh$_3$)$_3$, 4 ml of a 0.02M 1,3-diaminopropane (0.08 mmol) solution in isopropyl alcohol, and 12 ml of a 0.1M potassium hydroxide (1.2 mmol) solution in isopropyl alcohol in a nitrogen atmosphere, and the mixture was stirred at 0° C. for 3 hours under a hydrogen pressure of 50 atm.

The analysis of the reaction mixture by GC revealed that the conversion was 100% and the reaction selectivity was 98%. The reaction mixture was filtered, and the filtrate was concentrated under reduced pressure. The residue was dissolved in hexane, washed with a saturated sodium chloride aqueous solution, dried over anhydrous magnesium sulfate, and concentrated under reduced pressure. The resulting oily substance was distilled under reduced pressure to give 3.55 g (yield 85%) of (E)-(R)-2-ethyl-4-(2,2,3-trimethylcyclopent-3-en-1-yl)-2-buten-1-ol. As a result of GC, the product had a chemical purity of 95% and contained the (Z)-compound in a proportion of 2%.

Boiling point: 140 to 140.5° C. (12 mmHg); Specific rotation: $\alpha_D^{25}$=−2.9°; MS (m/z) 208(M$^+$), 193, 175, 161, 145, 135, 121, 109, 108, 95, 93, 79, 67; IR (film) (cm$^{-1}$): 3325, 2950, 1460, 1440, 1360, 1015; $^1$H-NMR (CDCl$_3$, δ ppm): 5.41 (1H, t, J=7.1 Hz, 3-CH═C), 5.22 (1H, brs), 4.05 (2H, brs, 1-CH$_2$), 2.28–2.17 (2H, m), 2.14 (2H, q, J=7.5 Hz, 5-CH$_2$), 2.04–1.95 (1H, m), 1.85–1.77 (2H, m), 1.61 (3H, s), 1.30 (1H, brs), 1.01 (3H, t, J=7.5 Hz, 6-Me), 1.00 (3H, s), 0.81 (3H, s)

Two-dimensional $^1$H-NMR:
   The $^1$H-1H-Cosy and $^1$H-$^1$H-NOESY spectra displayed a nucleo-overhouser effect (NOE), providing confirmation of the (E)-configuration.

REFERENCE EXAMPLE 5

The resulting (R)-2-ethyl-4-(2,2,3-trimethylcyclopent-3-en-1-yl)-2-buten-1-ol (1.0 g) having an (E)/(Z) ratio of 98/2 was dissolved in 2.0 ml of methanol and purified by recycle operation of a preparative HPLC. After recycling, 70 mg of a fraction having an (E)/(Z) ratio of about 1/1 was collected, which was dissolved in 1.2 ml of methanol, and again subjected to recycle operation to obtain the (Z)-compound and the (E)-compound in a yield of 4 mg each.

(Z)-Isomer: $^1$H-NMR (CDCl$_3$, δ ppm): 5.34 (1H, dd, J=7.1 and 7.7 Hz, 3-CH═C), 5.22 (1H, brs), 4.18 (2H, d, J=7.4 Hz, 1-CH$_2$), 2.0–2.3 (5H, m), 1.7–1.9 (2H, m), 1.60 (3H, m), 1.08 (1H, t, J=5.6 Hz), 1.04 (3H, t, J=7.4 Hz, 6-Me), 1.00 (3H, s), 0.80 (3H, s)

Two-dimensional $^1$H-NMR:
   The $^1$H-$^1$H-Cosy and $^1$H-$^1$H-NOESY spectra displayed the NOE effect, providing confirmation of the (Z)-configuration.

(E)-Isomer:
   The NMR spectrum of the (E)-compound was the same as the product before purification.

EXAMPLES 3 TO 7

Synthesis of (E)-(R)-2-Ethyl-4-(2,2,3-trimethylcyclopent-3-en-1-yl)-2-buten-1-ol In the same manner as in Example 2, the title compound was prepared by hydrogenating (E)-(R)-2-ethyl-4-(2,2,3-trimethylcyclopent-3-en-1-yl)-2-buten-1-al which was synthesized from (1S,5S)-α-pinene having an optical purity varying from 50% e.e. to 92% e.e.

The boiling points, MS, IR, and $^1$H-NMR data of all the products obtained were the same as those in Example 2. The optical purity and specific rotation of the products are shown in Table 1 below.

TABLE 1

| | Example No. | | | | |
|---|---|---|---|---|---|
| | 3 | 4 | 5 | 6 | 7 |
| Optical Purity (% e.e.) | 92 | 80 | 70 | 60 | 50 |
| Specific rotation (°) | −2.7 | −2.4 | −2.1 | −1.8 | −1.5 |

REFERENCE EXAMPLE 2

Synthesis of (E)-(S)-2-Ethyl-4-(2,2,3-trimethylcyclopent-3-en-1-yl)-2-buten-1-ol (E)-(S)-2-Ethyl-4-(2,2,3-trimethylcyclopent-3-en-1-yl)-2-buten-1-al synthesized from (1R,5R)-α-pinene having an optical purity of 97% e.e. (available from Aldrich) was hydrogenated in the same manner as in Example 2 to obtain the title compound.

Specific rotation: $\alpha_D^{25}$=+2.9°

The boiling point, MS, IR, and $^1$H-NMR data were the same as those of Example 2.

EXAMPLE 8

Synthesis of (E)-(R)-2-Ethyl-4-(2,2,3-trimethylcyclopent-3-en-1-yl)-2-buten-1-ol Hydrogenation reaction was carried out in the same manner as in Example 2, except that the reaction was carried out under a hydrogen pressure of 50 atm. at room temperature for 2 hours while stirring.

The results of GC revealed that the conversion was 100% and the reaction selectivity was 94%.

As is apparent from the comparison between Example 2 and Example 8, the reaction sensitivity is higher at 0° C. than at room temperature.

EXAMPLES 9 TO 15

Synthesis of (E)-(R)-2-Ethyl-4-(2,2,3-trimethylcyclopent-3-en-1-yl)-2-buten-1-ol Hydrogenation reaction was conducted in the same manner as in Example 2, except for changing the kinds and amount of the diamine and the base. The reaction results are shown in Table 2 below.

TABLE 2

| | Diamine | | Base | | Conversion (%) | Selectivity (%) |
|---|---|---|---|---|---|---|
| Example No. | Kind | Amount (ml*) | Kind | Amount (ml**) | | |
| 9 | 1,2-diaminoethane | 4 | KOH | 12 | 99.1 | 93.6 |
| 10 | 1,3-diaminopropane | 4 | KOH | 20 | 99.4 | 94.0 |
| 11 | 1,3-diaminopropane | 4 | NaOH | 12 | 99.2 | 94.3 |
| 12 | 1,3-diaminopropane | 4 | t-BuOK | 12 | 99.0 | 91.1 |
| 13 | 1,3-diaminopropane | 4 | MeONa | 12 | 99.1 | 89.4 |
| 14 | 1,3-diaminopropane | 8 | KOH | 12 | 99.2 | 94.2 |
| 15 | 1,3-diaminopropane | 16 | KOH | 12 | 99.3 | 95.8 |

Note:
*0.02M Solution in isopropyl alcohol.
**0.2M Solution in isopropyl alcohol.

EXAMPLES 16 TO 23

Synthesis of (E)-(R)-2-Ethyl-4-(2,2,3-trimethylcyclopent-3-en-1-yl)-2-buten-1-ol Hydrogenation reaction was conducted in the same manner as in Example 2, except for changing the kind and amount of the catalyst and the kind of the diamine and using a solvent as shown in Table 3 below. The reaction results are shown in Table 3.

TABLE 3

| Example No. | Catalyst | | Diamine | Solvent | Conversion (%) | Selectivity (%) |
|---|---|---|---|---|---|---|
| | Kind | Amount (mg) | | | | |
| 16 | RuCl$_2$(Ph$_3$P)$_3$ | 38.4 | 1,3-diaminopropane | toluene | 99.0 | 93.6 |
| 17 | " | " | 1,3-diaminopropane | diethyl ether | 99.0 | 94.0 |
| 18 | " | " | 1,3-diaminopropane | MeCN | 97.1 | 91.3 |
| 19 | " | " | 1,3-diaminopropane | hexane | 99.1 | 94.2 |
| 20 | " | " | 1,3-diaminopropane | tetrahydrofuran | 99.0 | 92.4 |
| 21 | " | 16.9 | 1,2-diaminoethane | isopropyl alcohol | 99.7 | 96.3 |
| 22 | " | 8.4 | 1,2-diaminoethane | isopropyl alcohol | 99.6 | 95.4 |

TABLE 3-continued

| Example No. | Catalyst Kind | Amount (mg) | Diamine | Solvent | Conversion (%) | Selectivity (%) |
|---|---|---|---|---|---|---|
| 23 | Ru-BINAP catalyst* | 38.4 | 1,3-diaminopropane | isopropyl alcohol | 97.5 | 85.5 |

Note:
*[Ru$_2$Cl$_4$(S)-Tol-BINAP)$_2$](NEt)$_3$

EXAMPLE 24

Synthesis of (E)-(R)-2-Propyl-4-(2,2,3-trimethylcyclopent-3-en-1-yl)-2-buten-1-ol In a 100 ml stainless steel autoclave were charged 6.60 g (0.03 mol) of (E)-(R)-2-propyl-4-(2,2,3-trimethylcyclopent-3-en-1-yl)-2-buten-1-al synthesized from (1S)-α-pinene having an optical purity of 97% e.e. in a conventional manner, 28.7 mg (0.03 mmol) of RuCl$_2$(PPh$_3$)$_3$, 2.4 ml of a 0.1M 1,2-diaminoethane (0.24 mmol) solution in isopropyl alcohol, and 15 ml of a 0.1M potassium hydroxide (1.5 mmol) solution in isopropyl alcohol in a nitrogen atmosphere, and the mixture was stirred at room temperature for 3 hours under a hydrogen pressure of 50 atm.

The analysis of the reaction mixture by GC revealed that the conversion was 100%. The reaction mixture was filtered, and the filtrate was concentrated under reduced pressure. The residue was dissolved in hexane, washed with a saturated sodium chloride aqueous solution, dried over anhydrous magnesium sulfate, and concentrated under reduced pressure. The resulting oily substance was distilled under reduced pressure to give 4.80 g (72%) of the title compound.

Boiling point: 137.5 to 138° C. (4 mmHg); Specific rotation: α$_D$$^{25}$=−0.23°; MS (m/z): 222(M$^+$), 207, 189, 161, 147, 135, 121, 108, 95, 81, 71; IR (film) (cm$^{-1}$): 3320, 2950, 1460, 1380, 1360, 1005; $^1$H-NMR (CDCl$_3$, δ ppm): 5.46 (1H, t, J=7.2 Hz), 5.22 (1H, brs), 4.02 (2H, brs), 2.16–2.29 (2H, m), 2.10 (2H, dd, J=7.2, 8.4 Hz), 1.99–2.01 (1H, m), 1.76–1.85 (2H, m), 1.60 (4H, brs), 1.44 (2H, q, J=7.6 Hz), 1.00 (3H, s), 0.92 (3H, t, J=7.2 Hz), 0.80 (3H, s)

EXAMPLE 25

Evaluation of Quality of Odor

The odor of the compounds prepared in Examples 1, 2 and 24 and Reference Examples 1 and 2 was evaluated by 7 specialized panelists in accordance with a triangle method (see T. E. Acree, et al., *J. Agric. Food Chem.*, Vol. 33, pp. 425–427 (1985)). The average of the threshold values given by 7 panelists is shown in Table 4 below.

TABLE 4

| Preparation Example No. | Configuration | Compound | Evaluation on Quality of Odor | Threshold Value* |
|---|---|---|---|---|
| Example 1 | (E)-(R) | [structure] | fresh and strong sandalwood oil odor associated with green trees | 51 |
| Reference Example 1 | (E)-(S) | [structure] | dry and weak sandalwood oil odor with a milky and floral note | 424 |
| Example 2 | (E)-(R) | [structure] | clean, bright and strong sandalwood oil odor with richness and a woody note | 0.85 |
| Reference Example 5 | (Z)-(R) | [structure] | inferior to the trans-compound in strength, lacking a woody note, and having butter-like sweetness | unmeasured |

TABLE 4-continued

| Preparation Example No. | Configuration | Compound | Evaluation on Quality of Odor | Threshold Value* |
|---|---|---|---|---|
| Reference Example 2 | (E)-(S) | | milky sandalwood oil odor with a cedar character | 44 |
| Example 24 | (E)-(R) | | soft and warm sandalwood oil odor, slightly weaker than the (E)-(R)-compound of Example 2 | unmeasured |

Note: *$10^{-12}$ M/1

EXAMPLE 26

Evaluation on Quality of Odor vs. Optical Purity

The quality of odor of the compounds obtained in Examples 2 to 7 was evaluated by 7 panelists. The results obtained are shown in Table 5 below.

COMPARATIVE EXAMPLE 1

(E)-(R)-2-Ethyl-4-(2,2,3-trimethylcyclopent-3-en-1-yl)-2-buten-1-ol having an optical purity of 40% e.e. was synthesized from (1R,5R)-α-pinene having an optical purity of 40% e.e. in the same manner as in Example 2. The odor of the resulting compound was evaluated by 7 panelists. The results obtained are shown in Table 5.

COMPARATIVE EXAMPLE 2

The odor of commercially available 2-ethyl-4-(2,2,3-trimethylcyclopent-3-en-1-yl)-2-buten-1-ol ((R)/(S)=30/70), Bacdanol (registered trademark, available from IFF) was evaluated by 7 panelists. The results obtained are shown in Table 5.

TABLE 5

| Example No. | Optical Purity (% e.e.) | Evaluation on Quality of Odor | Diffusibility | Volume and Depth |
|---|---|---|---|---|
| Example 2 | 97 | strong, clear, warm and creamy odor primarily having a woody note inherent to natural sandalwood | present | present |
| Example 3 | 92 | strong, clear, warm and creamy odor primarily having a woody note inherent to natural sandalwood | present | present |
| Example 4 | 80 | strong, clear, warm and creamy odor primarily having a woody note inherent to natural sandalwood | present | present |
| Example 5 | 70 | strong odor having a woody note inherent to natural sandalwood, slightly associated with green trees | present | present |
| Example 6 | 60 | strong odor having a woody note inherent to natural sandalwood, slightly associated with green trees | present | present |
| Example 7 | 50 | sandalwood oil odor, while slightly astringent compared with Examples 2 to 6 | present | present |
| Comparative Example 1 | 40 | sandalwood oil odor as in Examples 2 to 7 but lacking clearness with increased cedarwood-like astringency and sweetness | absent | absent |
| Comparative Example 2 | Bacdanol | less sandalwood-like than Examples 2 to 7 | absent | absent |

EXAMPLE 27

Floral Green and Musky Perfume Composition for Toiletries

A floral green and musky perfume composition for toiletries was prepared using the (E)-(R)-2-ethyl-4-(2,2,3-trimethylcyclopent-3-en-1-yl)-2-buten-1-ol prepared in Example 3 in accordance with the following formulation (unit: part by weight, hereinafter the same).

| | |
|---|---|
| Abbalide 50 BB (registered trademark)[1] | 50 |
| Bergamot oil | 50 |
| Cyclamenaldehyde[2] | 80 |
| Eugenol | 2 |
| γ-Methylionone[3] | 30 |
| Geraniol | 10 |
| Methyl dihydrojasmonate | 100 |
| Helional[4] | 80 |
| Hexylcinnamaldehyde | 30 |
| Phenylacetaldehyde | 2 |
| Kovanol (registered trademark)[5] | 100 |
| 1-Citronellol | 60 |
| 1-Citronelyl acetate | 3 |
| 1-Hydroxycitrolellal | 20 |
| Lilial[6] | 90 |
| Linalool | 30 |
| Linalyl acetate | 6 |
| Ethylene brassylate | 150 |
| Floralozone (registered trademark)[7] | 3 |
| Allylamyl glycolate | 1 |
| 2-Phenylethanol | 33 |
| (E)-(R)-2-Ethyl-4-(2,2,3-trimethylcyclopent-3-en-1-yl)-2-buten-1-ol obtained in Example 3 | 70 |
| Total: | 1000 |

[1] A 50% solution of 1,3,4,6,7,8-hexahydro-4,6,6,7,8,8-hexamethylcyclxopenta(γ)-2-benzopyran in benzyl benzoate (available from Bush Boak Allen)
[2] p-Isopropyl-α-methylhydrocinnamaldehyde
[3] 4-(2,2,6-Trimethyl-2-cyclohexen-1-yl)-3-methyl-3-buten-3-one
[4] α-Methyl-3,4-methylenedioxyhydrocinnamaldehyde
[5] 4(3)-(4-Hydroxy-4-methylpentyl)-3-cyclohexene-1-carboxyaldehyde (available from Takasago International Corporation)
[6] p-t-Butyl-α-methylhydrocinnamaldehyde
[7] p-Ethyl-α,α-dimethylhydrocinnamaldehyde (available from IFF)

EXAMPLE 28

Floral Perfume Composition for Soaps

A highly appealing floral perfume composition for soaps was prepared using the (E)-(R)-2-ethyl-4-(2,2,3-trimethylcyclopent-3-en-1-yl)-2-buten-1-ol prepared in Example 4 in accordance with the following formulation.

| | |
|---|---|
| Abbalide 50 BB (registered trademark) | 110 |
| Decyl aldehyde | 2 |
| Undecyl aldehyde | 6 |
| Benzyl salicylate | 30 |
| Linalool | 50 |
| 1-Citronellol | 130 |
| 1-Citronelylnitrile | 2 |
| Tricyclodecenyl propionate | 10 |
| α-Damascone | 1 |
| Ethyl vanillin | 3 |
| Hexylcinnamaldehyde | 140 |
| Indole[1] | 10 |
| Iso E Super (registered trademark)[2] | 100 |
| Coumarin | 20 |
| Heliopropine | 5 |
| Benzyl acetate | 80 |
| Lilial | 50 |
| γ-Methylionone | 40 |
| Orange oil (PERA BRAZIL) | 20 |
| 2-Phenylethanol | 90 |
| Rose oxide | 5 |
| 9-Decenol | 1 |
| Rosephenone | 10 |
| p-t-Butylcyclohexyl acetate | 40 |
| (E)-(R)-2-Ethyl-4-(2,2,3-trimethylcyclo-pent-3-en-1-yl)-2-buten-1-ol obtained in Example 4 | 45 |
| Total: | 1000 |

[1] 10% Dipropylene glycol solution
[2] 7(6)-Acetyl-1,2,3,4,5,6,7,8-octahydro-1,1,6,7-tetraethylnaphthalene (available from IFF)

EXAMPLE 29

Floral Perfume Composition for Shampoos

A highly appealing floral perfume composition for shampoos was prepared using the (E)-(R)-2-ethyl-4-(2,2,3-trimethylcyclopent-3-en-1-yl)-2-buten-1-ol prepared in Example 4 in accordance with the following formulation:

| | |
|---|---|
| γ-Undecalactone[1] | 15 |
| Ambroxan (registered trademark)[2,3] | 1 |
| Benzyl acetate | 50 |
| Bergamot oil | 50 |
| Citronellol | 40 |
| Ethyl (1S,6R)-2,2,6-trimethylcyclohexanecarboxylate | 5 |
| Ethyl acetoacetate[3] | 10 |
| Ethyl vanillin | 2 |
| Eugenol | 15 |
| γ-Methylionone | 17 |
| Methyl dihydrojasmonate | 30 |
| Helional (registered trademark)[4] | 8 |
| Heliotropin | 20 |
| Hexylcinnamaldehyde | 140 |
| Iso E Super (registered trademark) | 30 |
| Kovanol (registered trademark) | 50 |
| Lemon oil (produced in California) | 200 |
| cis-3-Hexenyl acetate | 5 |
| Allylamyl glycolate | 5 |
| Linalool | 40 |
| Methyl anthranilate | 10 |
| Ethylene brassylate | 10 |
| n-Hexyl salicylate | 50 |
| Oak Moss No. 1[5] | 5 |
| p-Cresyl methyl ether | 2 |
| 2-Phenylethanol | 70 |
| Tonalid (registered trademark)[6] | 50 |
| 2,4-Di-t-butylcyclohexanone | 20 |
| (E)-(R)-2-Ethyl-4-(2,2,3-trimethylcyclopent-3-en-1-yl)-2-buten-1-ol obtained in Example 4 | 50 |
| Total: | 1000 |

[1] 1% Dipropylene glycol solution
[2] Decahydro-3a,6,6,9a-tetramethylnaphtho[1,2-b]furan (available from Henkel)
[3] 10% Dipropylene glycol solution
[4] α-Methyl-3,4-methylenedioxyhydrocinnamaldehyde (available from IFF)
[5] Methyl 2,4-dihydroxy-3,6-dimethylbenzoate (produced by Takasago International Corporation)
[6] 6-Acetyl-1,1,2,4,4,7-hexamethyltetralin (available from Polaks Eurutal Workobv).

COMPARATIVE EXAMPLE 3

A floral perfume composition was prepared using (E)-(R)-2-ethyl-(2,2,3-trimethylcyclopent-3-en-1-yl)-2-buten-1-ol obtained in Example 2 or, for comparison, Bacdanol (registered trademark; 2-ethyl-4-(2,2,3-trimethylcyclopent-3-en-1-yl)-2-buten-1-ol; (R)/(S)=30/70) according to the following formulation.

| | |
|---|---|
| Bergamot oil | 20 |
| Linalool | 100 |
| Benzyl acetate | 70 |
| Phenylacetaldehyde[1] | 50 |
| Dimethylbenzylcarbinol | 20 |
| 1-Hydroxycitronellal | 40 |
| 1-Citronellol | 80 |
| Geraniol | 50 |
| Kovanol (registered trademark) | 145 |
| Helional | 70 |
| Lilial | 90 |
| Cyclamenaldehyde | 70 |
| Hexylcinnamaldehyde | 70 |
| 2-Phenylethanol | 10 |
| Methyl dihydrojasmonate | 20 |
| Eugenol | 10 |
| Indol[1] | 20 |
| Ethylene brassylate | 15 |
| (E)-(R)-2-Ethyl-4-(2,2,3-trimethylcyclopent-3-en-1-yl)-2-buten-1-ol obtained in Example 2 or Bacdanol | 50 |
| Total: | 1000 |

Note:
[1] 10% benzyl benzoate solution

The quality of the odor of the two perfume compositions was evaluated by 8 specialized panelists in accordance with a triangle method (one sample of the composition containing the (E-R)-compound and two samples of the composition containing Bacdanol were presented to panelists given with no preliminary information, and each panelist chose a sample having the strongest sandalwood-like odor). Six out of 8 panelist chose the composition containing the (E-R)-compound.

REFERENCE EXAMPLE 3

Synthesis of (R)-MTPA Ester of (E)-(R)-2-Ethyl-4-(2,2,3-Trimethylcyclopent-3-en-1-yl)-2-buten-1-ol To 31.5 mg (151 μmol) of (E)-(R)-2-Ethyl-4-(2,2,3-trimethylcyclopent-3-en-1-yl)-2-buten-1-ol obtained in Example 2 were added 54.8 mg (234 μmol) of (R)-MTPA-Cl, 103.5 mg (502 μmol) of dicyclohexylcarbodiimide, and 1.0 g (12.6 mmol) of pyridine, and the mixture was stirred at room temperature for 20 hours. The reaction mixture was quenched in a 5% hydrochloric acid aqueous solution. The organic layer was extracted with hexane, and the released urea derivative was separated by filtration. The filtrate was washed successively with a 5% hydrochloric acid aqueous solution, a saturated sodium hydrogencarbonate aqueous solution, and a saturated sodium chloride aqueous solution, dried over anhydrous sodium sulfate, followed by filtration. The solvent was removed by evaporation, and the residue was purified by silica gel column chromatography using toluene as a solvent to obtain the title compound.

REFERENCE EXAMPLE 4

Synthesis of (R)-MTPA Ester of (E)-(S)-2-Ethyl-4-(2,2,3-trimethylcyclopent-3-en-1-yl)-2-buten-1-ol An (R)-MTPA ester of (E)-(S)-2-ethyl-4-(2,2,3-trimethylcyclopent-3-en-1-yl)-2-buten-1-ol was prepared from the (E)-(S)-2-ethyl-4-(2,2,3-trimethylcyclopent-3-en-1-yl)-2-buten-1-ol obtained in Reference Example 2 in the same manner as in Reference Example 3.

While the invention has been described in detail and with reference to specific examples thereof, it will be apparent to one skilled in the art that various changes and modifications can be made therein without departing from the spirit and scope thereof.

What is claimed is:

1. (E)-(R)-2-ethyl-4-(2,2,3-trimethylcyclopent-3-en-1-yl)-2-buten-1-ol, which has an optical purity of 50% e.e. or higher.

2. (E)-(R)-2-ethyl-4-(2,2,3-trimethylcyclopent-3-en-1-yl)-2-buten-1-ol of claim 1, which has an optical purity of 80% e.e. or higher.

3. A perfume composition comprising (E)-(R)-2-ethyl-4-(2,2,3-trimethylcyclopent-3-en-1-yl)-2-buten-1-ol, wherein said (E)-(R)-2-ethyl-4-(2,2,3-trimethylcyclopent-3-en-1-yl)-2-buten-1-ol has an optical purity of 50% e.e. or higher.

4. The perfume composition of claim 3, wherein said (E)-(R)-2-ethyl-4-(2,2,3-trimethylcyclopent-3-en-1-yl)-2-buten-1-ol has an optical purity of 80% e.e. or higher.

5. The perfume composition of claim 3, wherein the content of said (E)-(R)-2-ethyl-4-(2,2,3-trimethylcyclopent-3-en-1-yl)-2-buten-1-ol is 0.1 to 50% by weight based on the total composition.

6. The perfume composition of claim 4, wherein the content at said (E)-(R)-2-ethyl-4-(2,2,3-trimethylcyclopent-3-en-1-yl)-2-buten-1-ol is 0.1 to 50% by weight based on the total composition.

7. (E)-(R)-2-ethyl-4-(2,2,3-trimethylcyclopent-3-en-1-yl)-2-buten-1-ol of an optical purity of 50% e.e. or higher, obtained by hydrogenating (E)-(R)-2-ethyl-4-(2,2,3-trimethylcyclopent-3-en-1-yl)-2-buten-1-al in the presence of a ruthenium-phosphine complex as a catalyst, a base comprising an alkali metal or an alkaline earth metal and an amine.

8. (E)-(R)-2-ethyl-4-(2,2,3-trimethylcyclopent-3-en-1-yl)-2-buten-1-ol of an optical purity of 80% e.e. or higher, obtained by hydrogenating (E)-(R)-2-ethyl-4-(2,2,3-trimethylcyclopent-3-en-1-yl)-2-buten-1-al in the presence of a ruthenium-phosphine complex as a catalyst, a base comprising an alkali metal or an alkaline earth metal, and an amine.

9. A perfume composition comprising (E)-(R)-2-ethyl-4-(2,2,3-trimethylcyclopent-3-en-1-yl)-2-buten-1-ol of an optical purity of 50% e.e. or higher, which is obtained by hydrogenating (E)-(R)-2-ethyl-4-(2,2,3-trimethylcyclopent-3-en-1-yl)-2-buten-1-al in the presence of a ruthenium-phosphine complex as a catalyst, a base comprising an alkali metal or an alkaline earth metal and an amine.

10. A perfume composition comprising (E)-(R)-2-ethyl-4-(2,2,3-trimethylcyclopent-3-en-1-yl)-2-buten-1-ol of an optical purity of 80% e.e. or higher, which is obtained by hydrogenating (E)-(R)-2-ethyl-4-(2,2,3-trimethylcyclopent-3-en-1-yl)-2-buten-1-al in the presence of a ruthenium-phosphine complex as a catalyst, a base comprising an alkali metal or an alkaline earth metal and an amine.

11. Optically pure (E)-(R)-2-ethyl-4-(2,2,3-trimethylcyclopent-3-en-1-yl)-2-buten-1-ol.

12. A perfume composition comprising optically pure (E)-(R)-2-ethyl-4-(2,2,3-trimethylcyclopent-3-en-1-yl)-2-buten-1-ol.

13. The perfume composition of claim 12, wherein the content of said optically pure (E)-(R)-2-ethyl-4-(2,2,3-trimethylcyclopent-3-en-1-yl)-2-buten-1-ol is 0.1 to 50% by weight based on the total composition.

* * * * *

UNITED STATES PATENT AND TRADEMARK OFFICE
CERTIFICATE OF CORRECTION

PATENT NO.   : 5,994,291
DATED        : November 30, 1999
INVENTOR(S)  : Takashi AIDA et al.

It is certified that error appears in the above-identified patent and that said Letters Patent is hereby corrected as shown below:

Please correct the above patent as follows so that in TABLE 4 at columns 19 and 20 and at columns 21 and 22, the compounds used in Reference Example 1 and in Reference Example 2 have a <u>hashed</u> wedge bond, <u>not a solid</u> wedge bond.

Specifically in TABLE 4, at columns 19 and 20, the second compound in TABLE 4 which is to right of "Reference Example 1" and which currently reads:

"
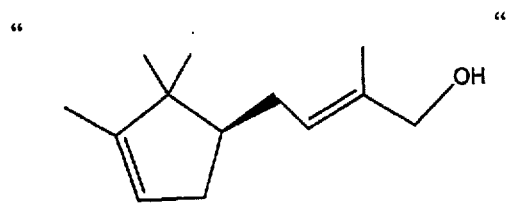
"

should be amended to read:

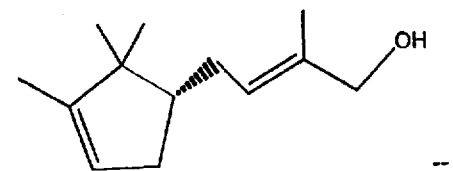
--                  -- and in TABLE 4 at columns 21 and 22, the fifth compound in TABLE 4 which is the first compound at the top of columns 21 and 22 and which is to the right of "Reference Example 2"

UNITED STATES PATENT AND TRADEMARK OFFICE
CERTIFICATE OF CORRECTION

PATENT NO. : 5,994,291
DATED : November 30, 1999
INVENTOR(S) : Takashi AIDA et al.

It is certified that error appears in the above-identified patent and that said Letters Patent is hereby corrected as shown below:

and which currently reads:

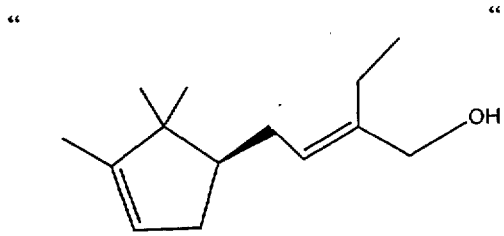

should be amended to read"

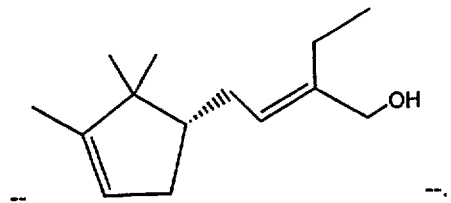

--.

Signed and Sealed this

First Day of May, 2001

Attest:

NICHOLAS P. GODICI

*Attesting Officer*  *Acting Director of the United States Patent and Trademark Office*